(12) United States Patent
Liu et al.

(10) Patent No.: US 11,034,984 B2
(45) Date of Patent: Jun. 15, 2021

(54) METHOD FOR IMPROVING YIELD OF ENZYMATIC PREPARATION OF BIODIESEL FROM GREASES

(71) Applicants: TSINGHUA UNIVERSITY, Beijing (CN); Beijing Cenway Bio-energy Technology Co., Ltd, Beijing (CN)

(72) Inventors: Dehua Liu, Beijing (CN); Wei Du, Beijing (CN); Luole Zhu, Hunan (CN); Jianchun Yang, Hunan (CN)

(73) Assignees: Tsinghua University, Beijing (CN); Beijing Cenway Bio-energy Technology Co., Ltd, Beijing (CN)

( * ) Notice: Subject to any disclaimer, the term of this patent is extended or adjusted under 35 U.S.C. 154(b) by 0 days.

(21) Appl. No.: 14/758,123

(22) PCT Filed: Jan. 28, 2014

(86) PCT No.: PCT/CN2014/000131
§ 371 (c)(1),
(2) Date: Jun. 26, 2015

(87) PCT Pub. No.: WO2014/101902
PCT Pub. Date: Jul. 3, 2014

(65) Prior Publication Data
US 2015/0353969 A1 Dec. 10, 2015

(30) Foreign Application Priority Data
Dec. 28, 2012 (CN) .......................... 201210585171.6

(51) Int. Cl.
*C12P 7/64* (2006.01)
*C12N 9/20* (2006.01)

(52) U.S. Cl.
CPC ................ *C12P 7/649* (2013.01); *C12N 9/20* (2013.01); *Y02E 50/10* (2013.01)

(58) Field of Classification Search
CPC combination set(s) only.
See application file for complete search history.

(56) References Cited

U.S. PATENT DOCUMENTS

2014/0123544 A1 * 5/2014 Du .......................... C10L 1/026
44/307

FOREIGN PATENT DOCUMENTS

| AU | 2011362409 A1 * | 10/2013 | ................ C10G 3/00 |
| CN | 101358216 A * | 8/2008 | ................ C12P 7/64 |

(Continued)

OTHER PUBLICATIONS

WO 2014/101902—RO-159 (PCT Rule 26.bis3) decision (Chinese).*

(Continued)

*Primary Examiner* — Sea C. Barron
(74) *Attorney, Agent, or Firm* — Knobbe Martens Olson & Bear LLP

(57) ABSTRACT

Provided in the present invention is a method for improving the yield of enzymatic preparation of biodiesel from greases, comprising: during enzymatic reaction of short-chain alcohols with greases to prepare biodiesel, introducing online dehydration steps, which lead the volatile gases in the enzyme reactor to enter into the low-temperature absorption tank, and the dehydrated gases flow back into the enzyme reactor. The formation of gas-circulation can constantly bring the moisture inside the enzyme reactor out.

8 Claims, 1 Drawing Sheet

(56) References Cited

FOREIGN PATENT DOCUMENTS

| CN | 101358216 A | | 2/2009 | |
|---|---|---|---|---|
| CN | 101932717 A | | 12/2010 | |
| CN | 102021207 A | | 4/2011 | |
| CN | 102676304 A | | 9/2012 | |
| WO | WO-2012/106701 | * | 8/2012 | ................ C12P 7/64 |

OTHER PUBLICATIONS

WO 2014/101902—RO-159 (PCT Rule 26.bis3) decision (English Translation).*

Jeong et al. Enzymatic esterification reaction in organic media with continuous water stripping: effect of water content on reactor performance. Biotechnology Techniques (1997), v11 (12), p. 853-858. (Year: 1997).*

Gofferjé et al. Enzyme-assisted deacidification of Jatropha crude oil by statistical design of experiments. Eur. J. Lipid Sci. Technol. 2014, 116, 1421-1431. (Year: 2014).*

Hama et al. Process engineering and optimization of glycerol separation in a packed-bed reactor for enzymatic biodiesel production. Bioresource Technology 102 (2011) 10419-10424. (Year: 2011).*

Clark et al. Biodiesel transesterification kinetics monitored bypH measurement. Bioresource Technology 136 (2013) 771-774. (Year: 2013).*

Chen, J.Z., et al., A Robust Process for Lipase-Mediated Biodiesel Production From Microalgae Lipid, RSC Advances 6:48515-48522, 2016.

Wang, J., et al., Lipase-Catalyzed Esterification of High Acid Value Waste Oil to Produce Biodiesel With Diesel Oil as Solvent, Journal of Fuel Chemistry and Technology 36(3), Jun. 2008, p. 291-296.

* cited by examiner

METHOD FOR IMPROVING YIELD OF ENZYMATIC PREPARATION OF BIODIESEL FROM GREASES

TECHNICAL FIELD

The present invention relates to the filed of biochemical engineering, particularly, to a method for improving the yield of enzymatic preparation of biodiesel from greases.

BACKGROUND ART

Biodiesel, a new prospect of grease industry, is a long-chain fatty acid ester-based substance produced by biological greases as raw materials through transesterification or esterification, and it is a novel, nonpolluting, renewable energy. The biodiesel is superior to the petroleum diesel in the flash point, combustion efficacy, sulphur content, oxygen content, aromatic hydrocarbon content, and oxygen consumption for combustion, and other indexes thereof are considerable to that of petroleum diesel. Suspended particles, CO, sulfides and hydrocarbons in the exhaust from combustion are significantly reduced, and thus environmental friendliness is possessed. The study and use of the biodiesel have been widely concerned.

Recently, the biodiesel is produced mainly by the chemical method, which produces a corresponding fatty acid methyl ester or ethyl ester by transesterification using animal and vegetable greases and some low-carbon alcohols (methanol or ethanol) under the actions of alkaline or acidic catalysts. The preparation of biodiesel by the chemical method has the following inevitable drawbacks: (1) the contents of free fatty acids and water in greases as raw materials are strictly required; (2) the saponified matters to be generated easily in the alkaline method increases the viscosity of the reaction system and the difficulty in separation of glycerin, and in the acidic method, the temperature of reaction is higher, and the device is to be easily corroded; (3) in the chemical method, the amount of methanol as used exceeds drastically the molar ratio of the reaction, and the recovery of excessive methanol enhances the energy consumption in the process; (4) a large amount of waste liquids containing waste acids or waste alkalis are generated during the production, which severely pollutes the environment.

Synthesis of biodiesel by bio-enzymatic method has the advantages of mild reaction conditions, low energy consumptions for operation, no pollutant discharge, wide applicability to the greases as raw materials, and the like, and accords with the developing direction of green chemistry, and thus it has increasingly drawn people's attention. However, during catalysis of greases by lipase to prepare biodiesel, when the greases as raw materials have water contents of greater than 0.5% or free fatty acid contents of greater than 3%, the water contained in the greases as raw materials and the water produced from the reaction of free fatty acids with acyl receptor, methanol or ethanol, will influence the esterification, resulting in the final acid value of the product greater than 5 mg KOH/g oil. Nevertheless, the acid value of biodiesel product is currently required to be less than 0.5 mg KOH/g oil in the standard of biodiesel in America, European Union, and China. In order to allow the biodiesel product to meet the requirement of the quality of biodiesel in China and the world for the acid value, a complicated process of alkali neutralization is subsequently needed. This subsequent process of reducing the acid value with alkali neutralization will both influence the yield and quality of product, and result in problems such as environmental pollution and the like.

DISCLOSURE OF THE INVENTION

The object of the present invention is to provide a method for improving the yield of enzymatic preparation of biodiesel from greases and the quality of the product (reducing the acid value of the final product of biodiesel).

In order to achieve the object of the present invention, in the method for improving the yield of enzymatic preparation of biodiesel from greases in the present invention, during enzymatic reaction of short-chain alcohols with greases to prepare biodiesel, online dehydration steps are introduced, which lead the volatile gases in the enzyme reactor to enter into the low-temperature absorption tank, and the dehydrated gases flow back into the enzyme reactor. The formation of gas-circulation can constantly bring the moisture inside the enzyme reactor out, thereby improving the conversion rate of the reaction.

In the above method, the temperature of reaction is 40° C. to 45° C. in the enzyme reactor.

In the above method, the low-temperature absorption tank is a short-chain alcohol absorption tank at 0° C. to 25° C.

In the above method, the enzyme reactor is a one stage enzyme reactor or a multiple stage enzyme reactor.

In the above method, the enzyme used in the enzymatic reaction of short-chain alcohols with greases to prepare biodiesel is a lipase derived from *Candida antarctica, Thermomyces lanuginosus, Aspergillus niger, Aspergillus oryzae, Rhizomucor miehei, Rhizopus oryzae*, or the like.

In the above method, the short-chain alcohol is one or more of methanol, ethanol, propanol, butanol, or the like.

In the above method, the greases are biological greases. The biological greases are one or more of vegetable greases, animal greases or microbial greases. The vegetable greases are one or more of palm oil, soya bean oil, rape-seed oil, curcas oil, jatropha curcasl oil, corn oil, castor oil, peanut oil, cottonseed oil, rice bran oil, shinyleaf yellowhorn oil, or the like; the animal greases are one or more of fish oil, beef tallow, lard, mutton tallow or the like; and the microbial greases are yeast grease, microalgae grease, or the like.

In the above method, the greases are waste edible oils or tailings from the refining of greases. The waste edible oils are hogwash oil, gutter oil or the like. The tailings from the refining of grease are acidified oil or the like.

The present invention introduces firstly the online dehydration technique during the enzymatic preparation of biodiesel from greases to remove online the water in the greases as raw materials or the water produced by esterification, so as to improve conversion rate of the reaction and quality of the product. The online dehydration process may be performed during the preparation of biodiesel by one-step enzymatic reaction (FIG. 1), and may also be performed during partial enzymatic reactions of multi-step reactions (FIG. 2). Particularly, during the reaction, volatile gases in an enzyme reactor are drawn out from the top of the reactor into a low-temperature absorption tank containing short-chain alcohols. The moisture inside the reactor will be brought out by the volatile gases, and the moisture which is brought out is to be absorbed by low-temperature short-chain alcohols. The dehydrated gases are then pumped into the enzyme reactor via the bottom of the enzyme reactor by an air pump, and a gas-circulation is thus formed so that the moisture in the reaction system can be brought out and absorbed constantly. Such an online dehydration process is achieved primarily utilizing the good water absorption property of short-chain alcohols at low temperatures (0° C.-20° C.). After online dehydration, the water content in the final reaction system can be controlled to be below 500 ppm, and the acid value of the biodiesel product is lower than 0.5 mg KOH/g oil. This online dehydration process using short-chain alcohols simplifies significantly the operation process, and has good economic and environmental benefits.

THE BEST MODE TO CARRY OUT THE INVENTION

The following Examples are used to describe the present invention, but not to limit the scope of the present invention. Unless indicated otherwise, the technical means used in the Examples are the conventional means well known to the skilled in the art, and all raw materials as used are commercially available.

Example 1

Figure 1:
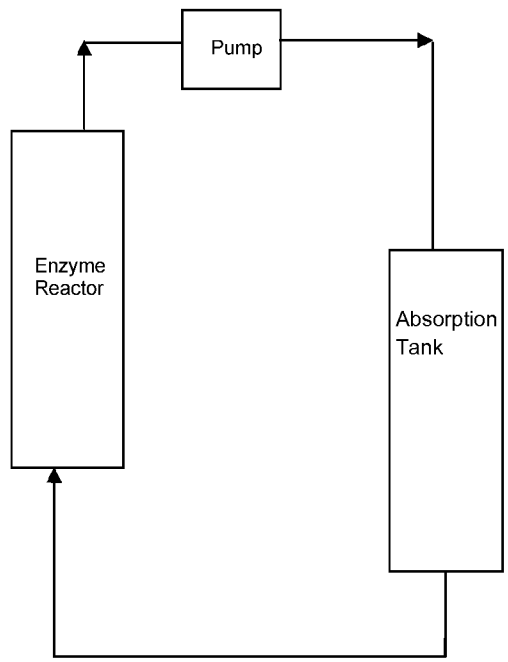
FIG. 1 is a schematic diagram of single stage enzymatic conversion of renewable greases with online dehydration to prepare the biodiesel according to the present invention.

Method for Improving the Yield of Enzymatic Preparation of Biodiesel from Greases 300 g palm oil and the methanol having a molar ratio of 1:1 of alcohol to oil were placed into an enzyme reactor, and the system contained 0.3% of water. An immobilized lipase derived from *Candida antarctica* having 200 standard enzyme activities based on unit grease mass was added, with a temperature of reaction controlled at 45° C. 150 g methanol with a water content of 400 ppm was placed into the short-chain alcohols absorption tank, with the temperature of the absorption tank controlled at 25° C. During the reaction, the online dehydration as shown in FIG. 1 was performed: volatile methanol gases in enzyme reactor were pumped out from the top of the reactor into a low-temperature absorption tank containing methanol; after the water brought out by the methanol gases was absorbed by the low-temperature absorption tank, the dehydrated dry methanol gases were pumped out and flowed back into the enzyme reactor from the bottom of the enzyme reactor by an air pump; so-formed gas-circulation can constantly bring the moisture inside the enzyme reactor out. The reaction was performed at 400 L/H of ventilatory volume for 12 hours, with the conversion rate of the reaction higher than 98%, the water content of the reaction liquid in the enzyme reactor being 500 ppm, and the acid value less than 0.5 mg KOH/g oil.

Example 2

Method for Improving the Yield of Enzymatic Preparation of Biodiesel from Greases 300 g jatropha curcasl oil and the ethanol having a molar ratio of 1:2 of alcohol to oil were placed into the enzyme reactor, and the system contained 0.8% of water. An immobilized lipase derived from *Aspergillus oryzae* having 100 standard enzyme activities based on unit grease mass and an immobilized lipase derived from *Candida antarctica* having 200 standard enzyme activities based on unit grease mass were added, with the temperature of reaction controlled at 45° C. 150 g ethanol with a water content of 400 ppm was placed into the short-chain alcohols absorption tank, with the temperature controlled at 20° C. During the reaction, the online dehydration as shown in FIG. 1 was performed: ethanol gases at the top of the enzyme reactor were pumped out from the top of the reactor into a low-temperature tank; the water brought out by the gases was absorbed by the low-temperature absorption tank; the dehydrated dry ethanol gases were pumped into the enzyme reactor from the bottom of the enzyme reactor by an air pump. The so-formed gas-circulation can constantly bring the moisture inside the enzyme reactor out. The reaction was performed at 400 L/H of ventilatory volume for 12 hours, with the conversion rate of the reaction higher than 98%, the water content of the reaction liquid in the enzyme reactor being 500 ppm, and the acid value less than 0.5 mg KOH/g oil.

Example 3

Method for Improving the Yield of Enzymatic Preparation of Biodiesel from Greases 300 g cottonseed oil and the methanol having a molar ratio of 1:1 of alcohol to oil were placed into the enzyme reactor, and the system contained 1% of water. An immobilized lipase derived from *Rhizomucor miehei* having 400 standard enzyme activities based on unit grease mass and an immobilized lipase derived from *Rhizopus oryzae* having 100 standard enzyme activities based on unit grease mass were added, with the temperature of reaction controlled at 40° C. 400 g methanol with a water content of 400 ppm was placed into the short-chain alcohols absorption tank, with the temperature controlled at 15° C. During the reaction, the online dehydration as shown in FIG. 1 was performed: methanol gases at the top of the enzyme reactor were pumped out from the top of the reactor into the low-temperature absorption tank; the water brought out by the gases was absorbed by the low-temperature absorption tank; the dehydrated dry methanol gases were pumped into the enzyme reactor from the bottom of the enzyme reactor by an air pump. The so-formed gas-circulation can constantly remove the moisture inside the enzyme reaction system and promote the reaction. The reaction was performed at 300 L/H of ventilatory volume for 10 hours, with the conversion rate of the reaction higher than 98%, the water content of the reaction liquid in the enzyme reactor reaching 560 ppm, and the acid value less than 0.5 mg KOH/g oil.

Example 4

Method for Improving the Yield of Enzymatic Preparation of Biodiesel from Greases 300 g jatropha curcasl oil and the ethanol having a molar ratio of 1:0.5 of alcohol to oil were placed into the enzyme reactor, and the system contained 0.3% of water. An immobilized lipase derived from *Aspergillus oryzae* having 100 standard enzyme activities based on unit grease mass and an immobilized lipase derived from *Candida antarctica* having 200 standard enzyme activities based on unit grease mass were added, with the temperature of reaction controlled at 45° C. 150 g ethanol was placed into the short-chain alcohols absorption tank, with the temperature controlled at 20° C. During the reaction, the online dehydration as shown in FIG. 1 was performed: ethanol gases at the top of the enzyme reactor were pumped out from the top of the reactor into the low-temperature absorption tank; the water in the gases was absorbed by the low-temperature ethanol; the dehydrated dry ethanol gases were pumped into the enzyme reactor from the bottom of the enzyme reactor by an air pump. The so-formed gas-circulation can constantly remove the moisture inside the reaction liquid, so as to effectively promote the esterification of the fatty acid with ethanol. The reaction was performed at 400 L/H of ventilatory volume for 12 hours, with the conversion rate of the reaction higher than 98%, the water content of the reaction liquid in the enzyme reactor reaching 560 ppm, and the acid value less than 0.5 mg KOH/g oil.

Example 5

Figure 2:
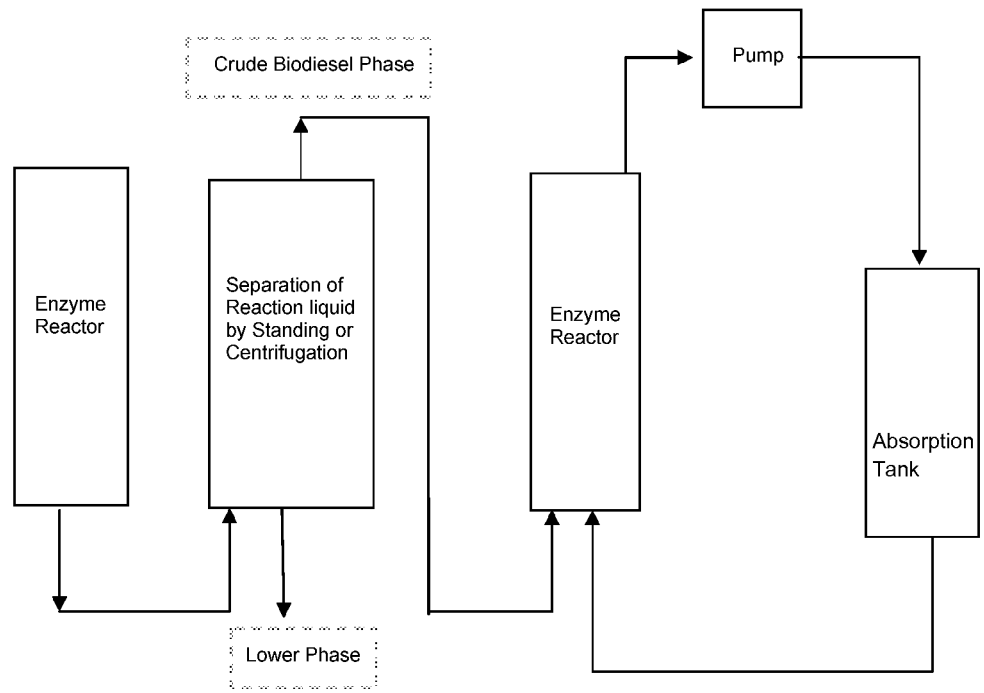
FIG. 2 is a schematic diagram of multiple stage enzymatic conversion of renewable greases with online dehydration to prepare the biodiesel according to the present invention.

Method for Improving the Yield of Enzymatic Preparation of Biodiesel from Greases Methanol and soya bean oil with a molar ratio of 4.5:1 were placed into the enzyme reactor, and the system contained 3% of water. A liquid lipase derived from *Candida antarctica* having 400 standard enzyme activities based on unit grease mass was added, with the temperature controlled at 40° C. The methanol was added over 4 hours at a uniform speed. After 7 hours of reaction, the glycerin and crude biodiesel phase were separated by standing. 335 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 0.04% was placed into the short-chain alcohols absorption tank, with the temperature of the methanol controlled at 5° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump, and fully in contact with the reaction liquid. The so-formed gas-circulation would constantly remove the moisture inside the reaction liquid, and promote the esterification of the fatty acid with methanol. The reaction was performed at 400 L/H of ventilatory volume for 3 hours, with the conversion rate of the reaction higher than 98%, the water content of the reaction liquid in the enzyme reactor reaching 123 ppm, and the acid value reaching 0.24 mg KOH/g oil.

Example 6

Method for Improving the Yield of Enzymatic Preparation of Biodiesel from Greases Methanol and microalgae grease with a molar ratio of 4.5:1 were placed into the enzyme reactor, and the system contained 3% of water. A liquid lipase derived from *Candida antarctica* having 400 standard enzyme activities based on unit grease mass was added, with the temperature controlled at 45° C. The methanol was added over 4 hours at a uniform speed. After 7 hours of reaction, the glycerin and crude biodiesel phase were separated by centrifugation. 335 g crude biodiesel was placed into the enzyme reactor for reaction, and an immobilized lipase derived from *Candida antarctica* having 200 standard enzyme activities based on unit grease mass was added, with the temperature of reaction controlled at 25° C. 395 g methanol with a water content of 0.55% was placed into the short-chain alcohols absorption tank, with the temperature of the methanol controlled at 11° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the esterification of the fatty acid with methanol. The reaction was performed at 400 L/H of ventilatory volume for 4 hours, with the conversion rate of the reaction higher than 98%, the water content of the reaction liquid in the enzyme reactor reaching 160 ppm, and the acid value reaching 0.26 mg KOH/g oil.

Example 7

Method for Improving the Yield of Enzymatic Preparation of Biodiesel from Greases Methanol and yeast grease with a molar ratio of 5:1 were placed into the enzyme reactor, and the system contained 5% of water. A liquid lipase derived from *Candida antarctica* having 400 standard enzyme activities based on unit grease mass was added, with the temperature controlled at 45° C. The methanol was added over 4 hours at a uniform speed. After 8 hours of reaction, the glycerin and crude biodiesel phase were separated by centrifugation. 335 g crude biodiesel was placed into the enzyme reactor for reaction, and an immobilized lipase derived from *Candida antarctica* having 200 standard enzyme activities based on unit grease mass was added, with the temperature controlled at 23° C. 336 g methanol with a water content of 5.8% was placed into the short-chain alcohols absorption tank, with the temperature of the methanol controlled at 5° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the esterification of the fatty acid with methanol. The reaction was performed at 400 L/H of ventilatory volume for 4 hours, with the conversion rate of the reaction higher than 98%, the water content of the reaction liquid in the enzyme reactor reaching 186 ppm, and the acid value reaching 0.46 mg KOH/g oil.

Example 8

Method for Improving the Yield of Enzymatic Preparation of Biodiesel from Greases Propanol and fish oil with a molar ratio of 4.5:1 were placed into the enzyme reactor, and the system contained 10% of water. A liquid lipase derived from *Candida antarctica* having 400 standard enzyme activities based on unit grease mass was added, with the temperature controlled at 45° C. The propanol was added over 6 hours at a uniform speed. After 14 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 30° C. 400 g propanol with a water content of 500 ppm was placed into the short-chain alcohols absorption tank, with the temperature of the propanol controlled at 11° C. During the reaction, the online dehydration as shown in FIG. 2 was performed: propanol gases at the top of the enzyme reactor were pumped out from the top of the reactor into the low-temperature absorption tank; the water in the gases was absorbed by the low-temperature propanol; the dehydrated dry propanol gases were pumped into the enzyme reactor from the bottom of the enzyme reactor by an air pump. The so-formed gas-circulation would constantly bring the moisture inside the reaction system out, so as to promote the reaction. The reaction was performed at 400 L/H of ventilatory volume for 4 hours, with the conversion rate of the reaction higher than 98%, the water content of the reaction liquid in the enzyme reactor reaching 188 ppm, and the acid value reaching 0.32 mg KOH/g oil.

Example 9

Method for Improving the Yield of Enzymatic Preparation of Biodiesel from Greases Butanol and beef tallow with a molar ratio of 4.5:1 were placed into the enzyme reactor, and the system contained 10% of water. A liquid lipase derived from *Candida antarctica* having 400 standard enzyme activities based on unit grease mass was added, with the temperature controlled at 45° C. The butanol was added over 6 hours at a uniform speed. After 15 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 30° C. 400 g butanol with a water content of 500 ppm was placed into the short-chain alcohols absorption tank, with the temperature of the butanol controlled at 11° C. During the reaction, the online dehydration as shown in FIG. 2 was performed: butanol gases at the top of the enzyme reactor were pumped out from the top of the reactor into the low-temperature absorption tank; the water in the gases was absorbed by the low-temperature butanol; the dehydrated dry butanol gases were pumped into the enzyme reactor from the bottom of the enzyme reactor by an air pump. The so-formed gas-circulation would constantly remove the moisture inside the reaction liquid, so as to promote the reaction. The reaction was performed at 400 L/H of ventilatory volume for 4 hours, with the conversion rate of the reaction higher than 98%, the water content of the reaction liquid in the enzyme reactor reaching 196 ppm, and the acid value reaching 0.30 mg KOH/g oil.

Example 10

Method for Improving the Yield of Enzymatic Preparation of Biodiesel from Greases Methanol and acidified oil with a molar ratio of 4.5:1 were placed into the enzyme reactor, and the system contained 10% of water. A liquid lipase derived from *Candida antarctica* having 400 standard enzyme activities based on unit grease mass was added, with the temperature controlled at 35° C. The methanol was added over 6 hours at a uniform speed. After 8 hours of reaction, the glycerin and crude biodiesel phase were separated by standing. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 4.1% was placed into the short-chain alcohols absorption tank, with the temperature of the methanol controlled at 5° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the reaction. The reaction was performed at 400 L/H of ventilatory volume for 4 hours, with the conversion rate of the reaction higher than 98%, the water content of the reaction liquid in the enzyme reactor reaching 120 ppm, and the acid value reaching 0.30 mg KOH/g oil.

Example 11

Method for Improving the Yield of Enzymatic Preparation of Biodiesel from Greases Methanol and corn oil with a molar ratio of 4.5:1 were placed into the enzyme reactor, and the system contained 10% of water. A liquid lipase derived from *Candida antarctica* having 400 standard enzyme activities based on unit grease mass was added, with the temperature controlled at 45° C. The methanol was added over 4 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 4.55% was placed into the short-chain alcohols absorption tank, with the temperature of the methanol controlled at 5° C. During the reaction, the online dehydration as shown in FIG. 2 was performed: methanol gases at the top of the enzyme reactor were pumped out from the top of the reactor into the low-temperature absorption water tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the reaction. The reaction was performed at 400 L/H of ventilatory volume for 4 hours, with the conversion rate of the reaction higher than 98%, the water content of the reaction liquid in the enzyme reactor reaching 146 ppm, and the acid value reaching 0.33 mg KOH/g oil.

Example 12

Method for Improving the Yield of Enzymatic Preparation of Biodiesel from Greases Methanol and oleic acid with a molar ratio of 4.5:1 were placed into the enzyme reactor, and the system contained 7.5% of water. A liquid lipase derived from *Candida antarctica* having 400 standard enzyme activities based on unit grease mass was added, with the temperature controlled at 45° C. The methanol was added over 4 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 5° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the reaction. The reaction was performed at 400 L/H of ventilatory volume for 4 hours, with the conversion rate of the reaction higher than 98%, the water content of the reaction liquid in the enzyme reactor reaching 156 ppm, and the acid value reaching 0.30 mg KOH/g oil.

Example 13

Method for Improving the Yield of Enzymatic Preparation of Biodiesel from Greases Methanol and peanut oil with a molar ratio of 4.5:1 were placed into the enzyme reactor, and the system contained 5% of water. A liquid lipase derived from *Candida antarctica* having 400 standard enzyme activities based on unit grease mass was added, with the temperature controlled at 45° C. The methanol was added over 4 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 15° C. During the reaction, the online dehydration as shown in FIG. 2 was performed: methanol gases at the top of the enzyme reactor were pumped out from the top of the reactor into the low-temperature water absorbing tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the esterification of the fatty acid with methanol. The reaction was performed at 400 L/H of ventilatory volume for 4 hours, with the conversion rate of the reaction higher than 98%, the water content of the reaction liquid in the enzyme reactor reaching 213 ppm, and the acid value reaching 0.28 mg KOH/g oil.

Example 14

Method for Improving the Yield of Enzymatic Preparation of Biodiesel from Greases Methanol and shinyleaf yellowhorn oil with a molar ratio of 4.5:1 were placed into the enzyme reactor, and the system contained 5% of water. A liquid lipase derived from *Candida antarctica* having 400 standard enzyme activities based on unit grease mass was added, with the temperature controlled at 45° C. The methanol was added over 4 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 15° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid, so as to promote the reaction. The reaction was performed at 500 L/H of ventilatory volume for 4 hours, with the conversion rate of the reaction higher than 98%, the water content of the reaction liquid in the enzyme reactor reaching 231 ppm, and the acid value reaching 0.27 mg KOH/g oil.

Example 15

Method for Improving the Yield of Enzymatic Preparation of Biodiesel from Greases Methanol and rice bran oil with a molar ratio of 4.5:1 were placed into the enzyme reactor, and the system contained 5% of water. A liquid lipase derived from *Candida antarctica* having 400 standard enzyme activities based on unit grease mass was added, with the temperature controlled at 45° C. The methanol was added over 4 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 15° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump to form a gas-circulation. The so-formed gas-circulation would constantly remove the moisture inside the reaction liquid, so as to promote the reaction. The reaction was performed at 400 L/H of ventilatory volume for 4 hours, with the conversion rate of the reaction higher than 98%, the water content of the reaction liquid in the enzyme reactor reaching 193 ppm, and the acid value reaching 0.26 mg KOH/g oil.

Example 16

Method for Improving the Yield of Enzymatic Preparation of Biodiesel from Greases Methanol and castor oil with a molar ratio of 4.5:1 were placed into the enzyme reactor, and the system contained 5% of water. A liquid lipase derived from *Candida antarctica* having 300 standard enzyme activities based on unit grease mass was added, with the temperature controlled at 45° C. The methanol was added over 5 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 200 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 11° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump to form a gas-circulation, constantly removing the moisture inside the reaction liquid so as to promote the reaction. The reaction was performed at 400 L/H of ventilatory volume for 4 hours, with the conversion rate of the reaction higher than 98%, the water content of the reaction liquid in the enzyme reactor reaching 163 ppm, and the acid value reaching 0.42 mg KOH/g oil.

Example 17

Method for Improving the Yield of Enzymatic Preparation of Biodiesel from Greases Methanol and curcas oil with a molar ratio of 4.5:1 were placed into the enzyme reactor, and the system contained 10% of water. A liquid lipase derived from *Candida antarctica* having 200 standard enzyme activities based on unit grease mass was added, with the temperature controlled at 45° C. The methanol was added over 6 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 400 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 11° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump to form a gas-circulation, constantly removing the moisture inside the reaction liquid so as to promote the reaction. The reaction was performed at 400 L/H of ventilatory volume for 2.5 hours, with the conversion rate of the reaction higher than 98%, the water content of the reaction liquid in the enzyme reactor reaching 230 ppm, and the acid value reaching 0.22 mg KOH/g oil.

Example 18

Method for Improving the Yield of Enzymatic Preparation of Biodiesel from Greases Methanol and gutter oil with a molar ratio of 4.5:1 were placed into the enzyme reactor, and the system contained 10% of water. A liquid lipase derived from *Candida antarctica* having 200 standard enzyme activities based on unit grease mass was added, with the temperature controlled at 45° C. The methanol was added over 6 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 400 standard enzyme activities based on unit grease mass was added, with the temperature of reaction controlled at 25° C. 400 g methanol with a water content of 500 ppm was placed into the short-chain alcohols absorption tank, with the temperature of the methanol controlled at 5° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump to form a gas-circulation, constantly removing the moisture inside the reaction liquid so as to promote the reaction. The reaction was performed at 400 L/H of ventilatory volume for 3 hours, with the conversion rate of the reaction higher than 98%, the water content of the reaction liquid in the enzyme reactor reaching 170 ppm, and the acid value reaching 0.33 mg KOH/g oil.

Example 19

Method for Improving the Yield of Enzymatic Preparation of Biodiesel from Greases Methanol and cottonseed oil with a molar ratio of 4.5:1 were placed into the enzyme reactor, and the system contained 3% of water. A liquid lipase derived from *Candida antarctica* having 200 standard enzyme activities based on unit grease mass was added, with the temperature controlled at 45° C. The methanol was added over 6 hours at a uniform speed. After 8 hours of reaction, the glycerin and crude biodiesel phase were separated by centrifugation. 340 g crude biodiesel was placed into the enzyme reactor for reaction, and an immobilized lipase derived from *Candida antarctica* having 400 standard enzyme activities based on unit grease mass was added, with the temperature of reaction controlled at 25° C. 400 g methanol with a water content of 500 ppm and 40 g metal mesh packing were placed into the short-chain alcohols water absorbing tower, with the temperature of the methanol controlled at 11° C. During the reaction, the online dehydration as shown in FIG. 2 was performed: methanol gases at the top of the enzyme reactor were pumped out from the top of the reactor into the low-temperature absorption tank; the water in the gases was absorbed by the low-temperature methanol; the dehydrated dry methanol gases were pumped into the enzyme reactor from the bottom of the enzyme reactor by an air pump. The so-formed gas-circulation would constantly remove the moisture inside the reaction liquid. The reaction was performed at 400 L/H of ventilatory volume for 2.5 hours, with the conversion rate of the reaction higher than 98%, the water content of the reaction liquid in the enzyme reactor reaching 150 ppm, and the acid value reaching 0.21 mg KOH/g oil.

While general descriptions and specific embodiments have been used above to describe the present invention in detail, it is apparent to the skilled in the art that some modifications or improvements may be made to them based on the present invention. Therefore, these modifications or improvements as made without departing from the spirit of the present invention all belong to the scope claimed by the present invention.

INDUSTRIAL APPLICATION

The present invention has advantages in that: during the enzymatic preparation of biodiesel from greases by transesterification, one stage enzyme reactor or partial enzyme reactors in a multiple stage enzyme reactors is connected to a low-temperature absorption tank containing short-chain alcohols; volatile gases in an enzyme reactor are drawn out from the top of the reactor into the above low-temperature absorption tank; the dehydrated gases were pumped back into the enzyme reactor via the bottom of the enzyme reactor by an air pump; the so-formed gas-circulation enables the moisture in the enzyme reaction system to be brought out and absorbed constantly so as to achieve the purpose for increasing the conversion rate of the reaction and reducing the acid value of the product. The temperature of the absorption tank containing short-chain alcohols is controlled in the range from 0° C. to 25° C. After 3-12 hours of enzymatic reaction, the conversion rate from greases as raw materials to the biodiesel is greater than 98%, and the acid value of biodiesel as the final product is less than 0.5 mg KOH/g oil.

The invention claimed is:

1. A method for improving the yield of enzymatic preparation of biodiesel from greases with online dehydration, comprising:

enzymatically reacting short-chain alcohols with the greases in an enzyme reactor to prepare a crude biodiesel phase, separating glycerin from the crude biodiesel phase by a centrifugation, enzymatically reacting the short-chain alcohols with the crude biodiesel phase in the enzyme reactor to prepare biodiesel, circulating volatile gases of the short-chain alcohols produced in the enzyme reactor to enter into a low-temperature absorption tank which is separated from the enzyme reactor, dehydrating the volatile gases in the low temperature absorption tank, and circulating the dehydrated volatile gases back into the enzyme reactor; wherein the circulating and dehydrating of the volatile gases constantly brings moisture inside the enzyme reactor to outside of the enzyme reactor, so as to improve a conversion rate from the greases to the biodiesel in the reaction, wherein the absorption tank is a short-chain alcohols absorption tank, wherein the absorption tank has a lower temperature relative to a temperature of the enzymatic reaction, and wherein the lower temperature is 0° C. to 15° C., wherein the enzyme reactor is a multiple stage enzyme reactor, wherein the enzymatic reaction is performed for 4 hours or less with the conversion rate of higher than 98% and a acid value of the biodiesel of 0.33 mg KOH/g oil or less.

2. The method according to claim 1, wherein the enzymatically reacting of the short-chain alcohols with the crude biodiesel phase in the enzyme reactor is at a temperature from 40° C. to 45° C.

3. The method according to claim 1, wherein the enzyme used in the enzymatic reaction of short-chain alcohols with crude biodiesel phase to prepare biodiesel is a lipase derived from *Candida antarctica, Thermomyces lanuginosus, Aspergillus niger, Aspergillus oryzae, Rhizomucor miehei*, or *Rhizopus oryzae*.

4. The method according to claim 1, wherein the short-chain alcohols are one or more of methanol, ethanol, propanol, or butanol.

5. The method according to claim 1, wherein the greases are biological greases.

6. The method according to claim 5, wherein the biological greases are one or more of vegetable greases, animal greases or microbial greases.

7. The method according to claim 6, wherein the vegetable greases are one or more of palm oil, soya bean oil, rape-seed oil, curcas oil, jatropha curcasl oil, corn oil, castor oil, peanut oil, cottonseed oil, rice bran oil, or shinyleaf yellowhorn oil; the animal greases are one or more of fish oil, beef tallow, lard, or mutton tallow; and the microbial greases are yeast grease, or microalgae grease.

8. The method according to claim 1, wherein the greases are waste edible oils or tailings from the refining of greases.

* * * * *